US00PP37027P2

(12) United States Plant Patent
Hansoti

(10) Patent No.: US PP37,027 P2
(45) Date of Patent: Oct. 14, 2025

(54) ***SANSEVIERIA* PLANT NAMED 'Hansoti48'**

(50) Latin Name: *Sansevieria trifasciata*
Varietal Denomination: Hansoti48

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,540

(22) Filed: Dec. 23, 2024

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./382
CPC ..... A01H 6/12; A01H 5/12; A01H 5/02
See application file for complete search history.

*Primary Examiner* — Keith O. Robinson

(57) ABSTRACT

A new and distinct cultivar of *Sansevieria* plant named 'HANSOTI48' is disclosed, characterized by overall dark green leaves heavily marked with silver-green so that the overall impression is of a silvery green plant rosette. Distal 2-3 cm of each leaf is dark green with a long green tip. Leaf length is distinctly longer and narrower than in the parent cultivar, with mature leaves in typical 3-month-old plants being 14 to 16 cm long. The leaves show various shades of green colouration, with dark green leaves, largely covered with silvery green but with the typical *Sansevieria trifasciata* cross hatching subdued and less well marked. The new cultivar can be classified in the Hahnii *Sansevieria* Group. The new variety is a *Sansevieria*, typically produced as an ornamental plant.

11 Drawing Sheets

Latin name of the genus and species: *Sansevieria trifasciata.*

Variety denomination: 'HANSOTI48'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI48 '.

*Sansevieria* is a monocotyledonous plant with fleshy, succulent leaves which are available in a huge range of species, varieties and cultivars as an outdoor ornamental plant (under tropical conditions) or as indoor plants. Both, the parental 'Hahnii Jade Marginata' and the new cultivar 'Hansoti48' belong to the group of *Sansevieria trifasciata* called the "Hahnii *Sansevieria* Group" of short or dwarf cultivars all ultimately derived from the original *Sansevieria trifasciata* 'Hahnii' patented in 1941 (U.S. Plant Pat. No. 470), in contrast to the medium sized "Compact *Sansevieria* Group" with *Sansevieria trifasciata* 'Futura Superba' (unpatented) as the typical example, and the "Tall *Sansevieria* Group" of *Sansevieria trifasciata* cultivars with tall leaves up to 4 feet (1.25 meters) or taller and *Sansevieria trifasciata* 'Laurentii' (unpatented) as the typical example.

The new *Sansevieria* 'HANSOTI48' was discovered and selected by the inventor, Ashish Hansoti, as a single aberrant side shoot within a planting of *Sansevieria trifasciata* 'Hahnii Marginata', unpatented, a 'Hahnii' type of *Sansevieria* grown at a nursery in Village Vangani, District Thane, Maharashtra State in Western India. 'HANSOTI48' originated as a naturally-occurring mutation of the *Sansevieria trifasciata* variety 'Hahnii Jade Marginata' in May or June of 2019.

Both the parental 'Hahnii Jade Marginata' and the new cultivar 'Hansoti48' belong to the group of *Sansevieria trifasciata* called the "Hahnii *Sansevieria* Group" of short or dwarf cultivars all ultimately derived from the original *Sansevieria trifasciata* 'Hahnii' patented in 1941 (U.S. Plant Pat. No. 470), in contrast to the medium sized "Compact *Sansevieria* Group" with *Sansevieria trifasciata* 'Futura Superba', unpatented as the typical example, and the "Tall *Sansevieria* Group" of *Sansevieria trifasciata* cultivars with tall leaves up to 4 feet (1.25 meters) or taller and *Sansevieria trifasciata* 'Laurentii', unpatented as the typical example.

Asexual reproduction of the new *Sansevieria* cultivar by vegetative cuttings was first performed in early 2020 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI48', which in combination distinguish this *Sansevieria* as a new and distinct cultivar:

1. Overall dark green leaves heavily marked with silver-green so that the overall impression is of a silvery green plant rosette.
2. Distal 2-3 cm of each leaf is dark green with a long green tip. The typical longitudinal striations of *Sansevieria trifasciata* are subdued, somewhat diffuse but present as dark green bands.

3. The leaves are narrower and longer than the parent. Therefore, overall, the rosettes of 'Hansoti48' are taller than the parent.

Leaf length is distinctly longer and narrower than in the parent cultivar, with mature leaves in typical 3-month-old plants being 14 to 16 cm long. Leaf width is quite variable and the strongest, healthiest plants have the widest leaves—this is true across all *Sansevieria trifasciata* cultivars known to the inventor. This variation means leaf width can be anything from 4 cm to 6 cm wide depending on season, growing conditions and plant vigour and plant age. Typically, the leaves are of medium width and lanceolate with a firm, waxy texture. The blades are relatively thinner and softer than in the parent.

The new variety presents 9-12 leaves with an average of 11 full size, mature leaves per plant when it reaches its saleable size (about 3 months from rooted cutting) but over time it can grow and accumulate many more leaves and increase in overall height.

The new variety is moderately drought tolerant and adapts well to conditions of bright light or heavy shade (exterior and interior). The plant is liable to get scorched in full hot sun.

The leaves show various shades of green colouration, with dark green leaves, largely covered with silvery green but with the typical *Sansevieria trifasciata* cross hatching subdued and less well marked.

Each leaf has a dark green background close to RHS Green 139A. Superimposed on this are large silvery green areas close to Greyed-Green 191A. There is no variegation apart from these variations in green.

The backside of the leaves has a more uniform silver green coloration (RHS Greyed-Green 191B) with minimal dark green background showing in the proximal central area of each leaf. A uniform, thin dark green border of 1-2 mm width outlines each leaf on the backside.

Attached color pictures are a better guide to the complex leaf arrangement and the overall coloration and pattern rather than written descriptions.

PARENTAL COMPARISON

Plants of the new *Sansevieria* 'HANSOTI48' are similar to plants of the parental cultivar, however, 'HANSOTI48' differs in the characteristics described in Table 1.

TABLE 1

Comparison of Parental and the New variety 'Hansoti48'

| | Characteristic | Parent Cultivar 'Hahnii Jade Marginata' | New cv 'Hansoti48' |
|---|---|---|---|
| 1. | Leaf size & substance | 12 to 14 cm long. Leaves are thick, fleshy and brittle. | 14 to 16 cm long (Somewhat longer). Leaves are thinner, softer and more flexible. |
| 2. | Number of leaves | 8 to 11 leaves in a sale size plant | 9 to 12 leaves in a sale size plant of similar age (More leaves) |
| 3. | Variegation Pattern | Cream border on dark green leaves with typical *S. trifasciata* transverse banding. | Dark green leaves mostly covered with silvery green areas with relatively mild green horizontal bands that are equivalent to the transverse banding typical of *S. trifasciata*. |
| 4. | Border variegation | 2 to 15 mm wide cream band along edge of leaf | None - there is no border variegation. |
| 5. | Central Variegation | Basic green background and prominent transverse banding of light green as seen in most *S. trifasciata* cultivars. | No variegation and transverse banding much subdued. |

In essence, 'Hansoti48' is very different from the parental cultivar in being entirely green/silvery green with no cream or yellow variegation. However, this overall silvery green color with minimal cross striations is unusual amongst Hahnii Type *Sansevieria* and the pattern is attractive.

'Hansoti48' is also somewhat different in size and shape—the leaves are narrower and longer; subsequently, the rosette is taller. Individual leaves are distinctly thinner and softer than the thicker, fleshier and harder leaves of the parent, 'Hahnii Jade Marginata'.

COMMERCIAL COMPARATOR

Plants of the new *Sansevieria* 'HANSOTI48' are similar to the commercial variety *Sansevieria trifasciata* 'Frozen', U.S. Plant Pat. No. 29,345. Plants of the new *Sansevieria* 'HANSOTI48' differ from plants of the commercial cultivar in the characteristics described in Table 2.

TABLE 2

Comparison of similar variety 'Frozen' and the New variety 'Hansoti48'

| | Characteristic | Similar Cultivar 'Frozen' U.S. Plant Pat. No. 29,345 | New cv 'Hansoti48' |
|---|---|---|---|
| 1. | Leaf size | 25-30 cm long | 14 to 16 cm long (Much Shorter) |
| 2. | Number of leaves | 5 to 7 leaves - far fewer leaves. | 9 to 12 leaves - many more leaves. |
| 3. | Variegation Pattern | The plant has no variegation and is dark green with silvery green horizontal bands. This overall silvery green look with some dark green is common to the two plants. | Substantially shorter, more compact or dwarf rosette with dark green leaves mostly covered by silvery green overlay, occasional green bands. |
| 4. | Border variegation | None | None |
| 5. | Central Variegation | None | None |

BRIEF DESCRIPTION OF THE PHOTOGRAPHS

The accompanying photographs illustrate the overall appearance of the new *Sansevieria* cultivar 'HANSOTI48' showing the colors as true as is reasonably possible with colored reproductions of this type. Colors in the photographs may differ slightly from the color value cited in the detailed botanical description which accurately describe the color of 'HANSOTI48'.

These pictures illustrate the plant form which is the unique characteristic of 'HANSOTI48' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India.

Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

FIG. 1, FIG. 2 and FIG. 3: Show a three-to four-month-old plant (from rooted liner) of *Sansevieria* 'HANSOTI48' in a 12 cm diameter pot from various angles.

FIG. 4, FIG. 5 and FIG. 6: Shows various views of a tray full (with 14 plants in 10 cm pots) of 'Hansoti48' plants—the uniformity across numerous plants of the same age (10 to 12 weeks) and in the same pot is obvious.

Figure 1:
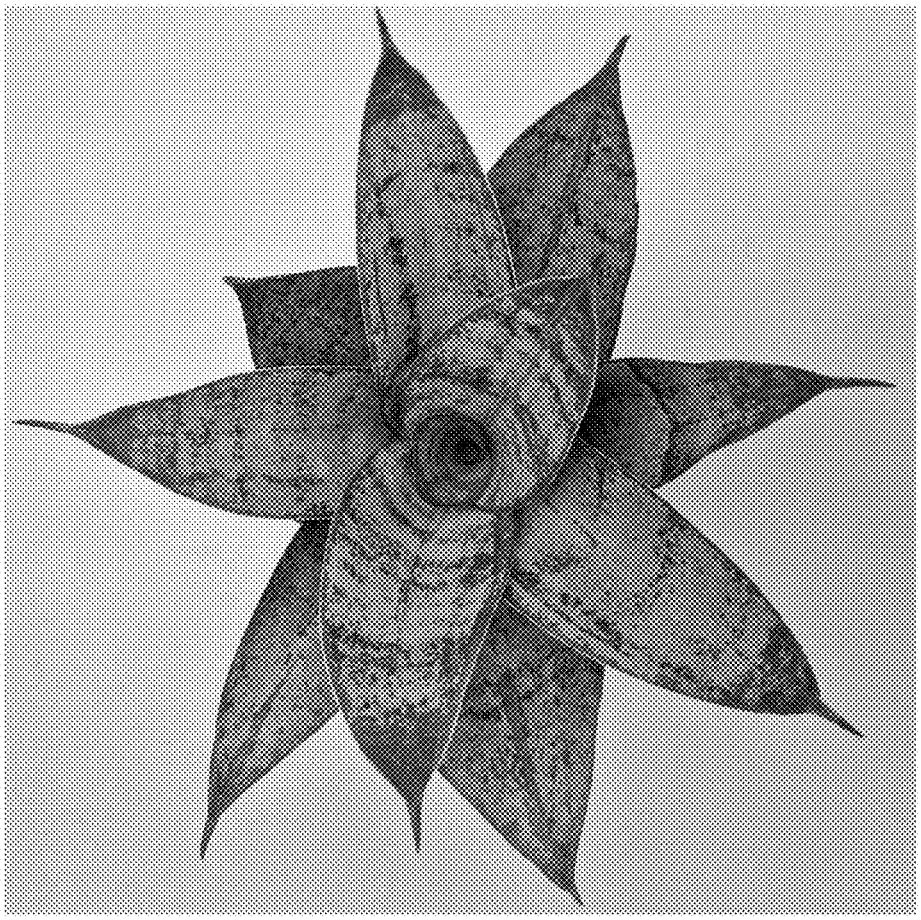
Figure 2:
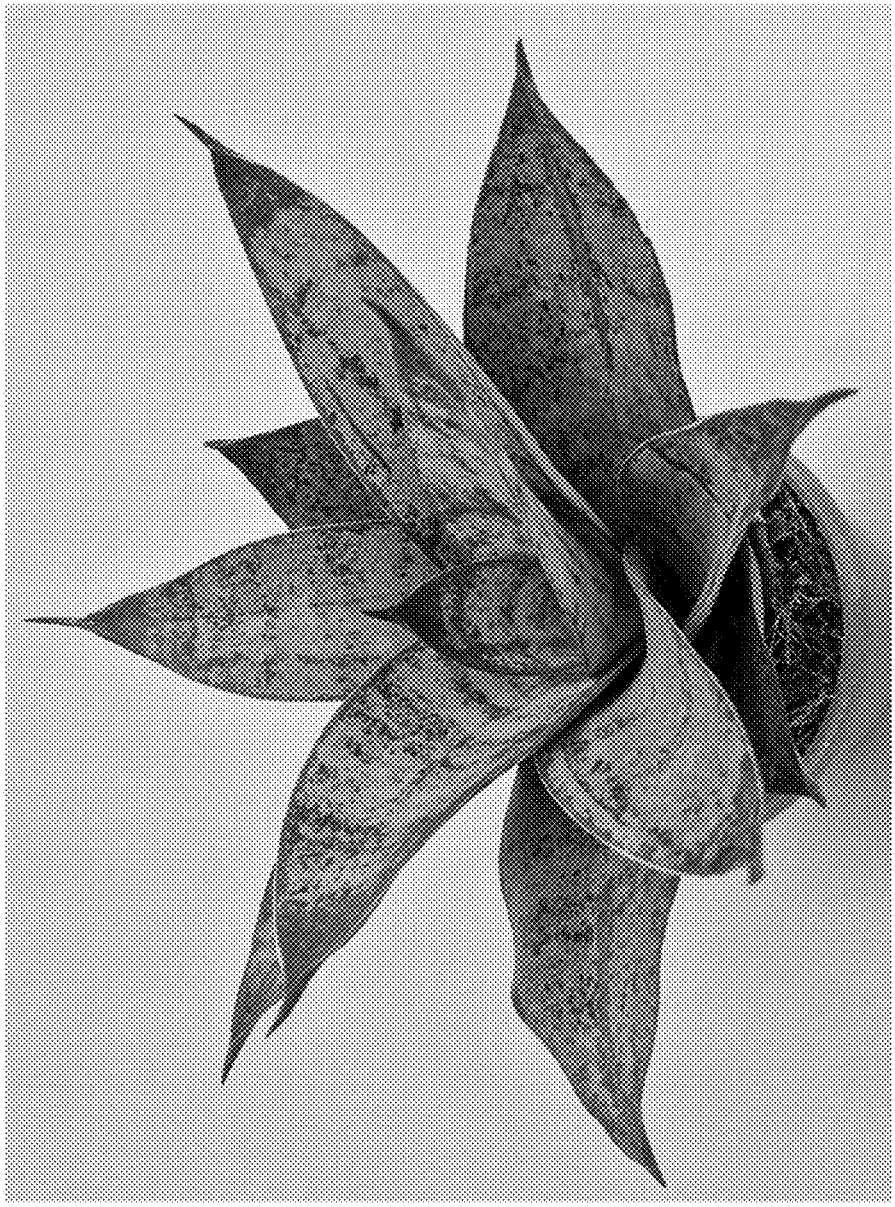
Figure 3:
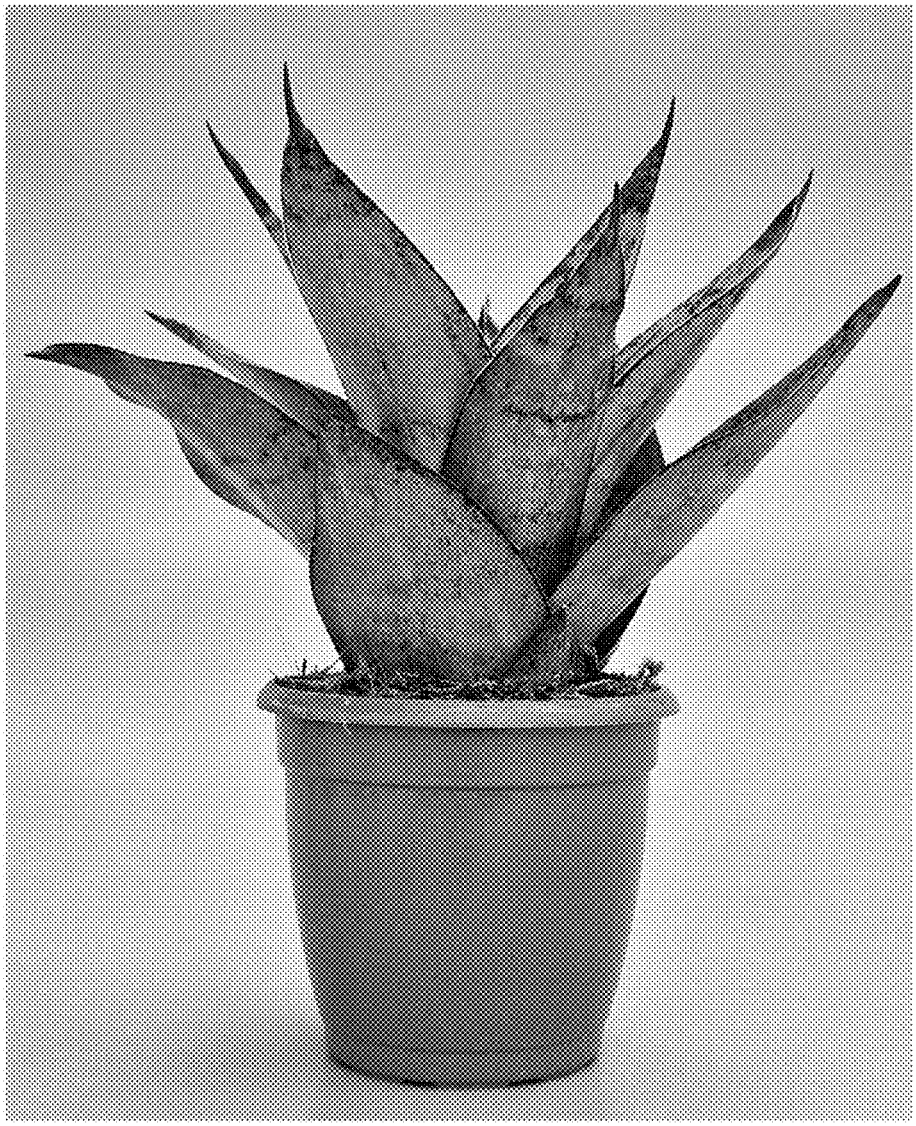
Figure 4:
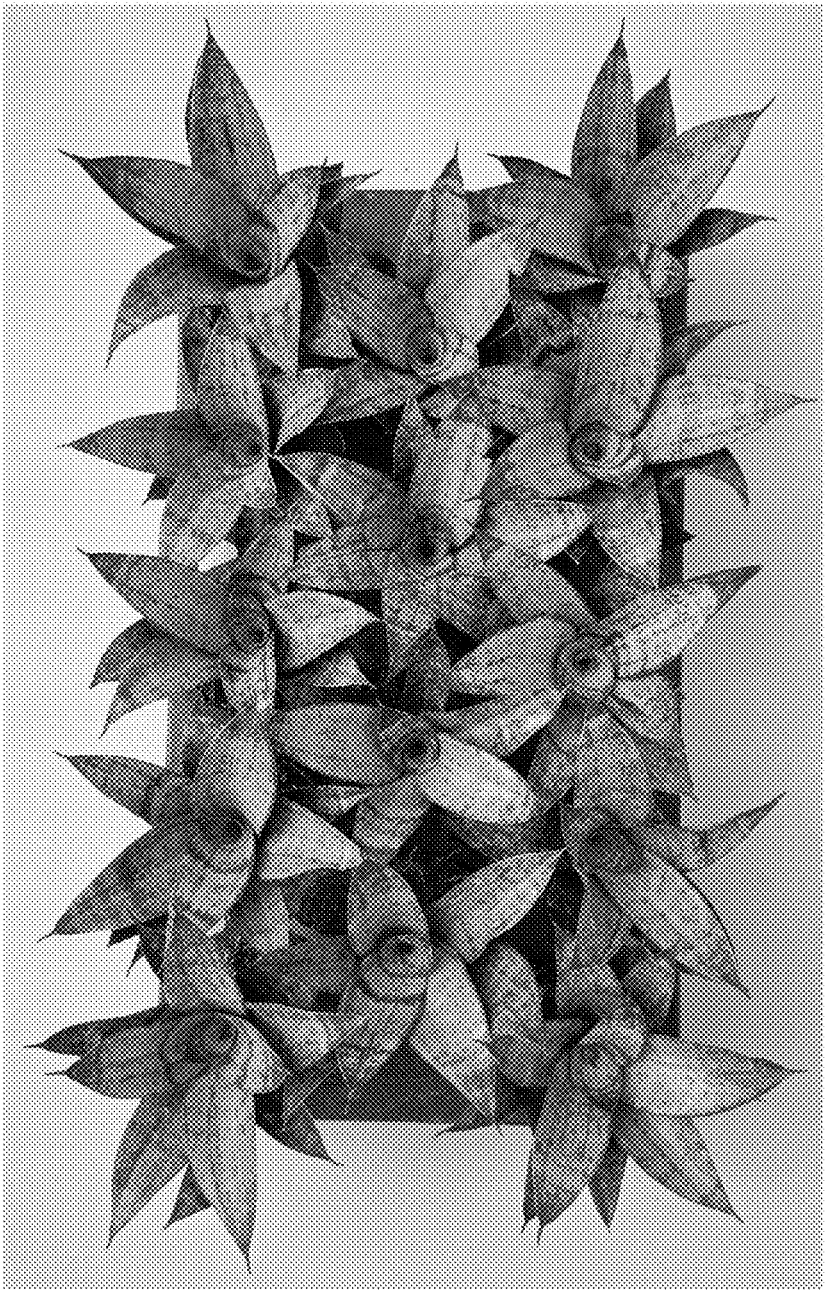
Figure 5:
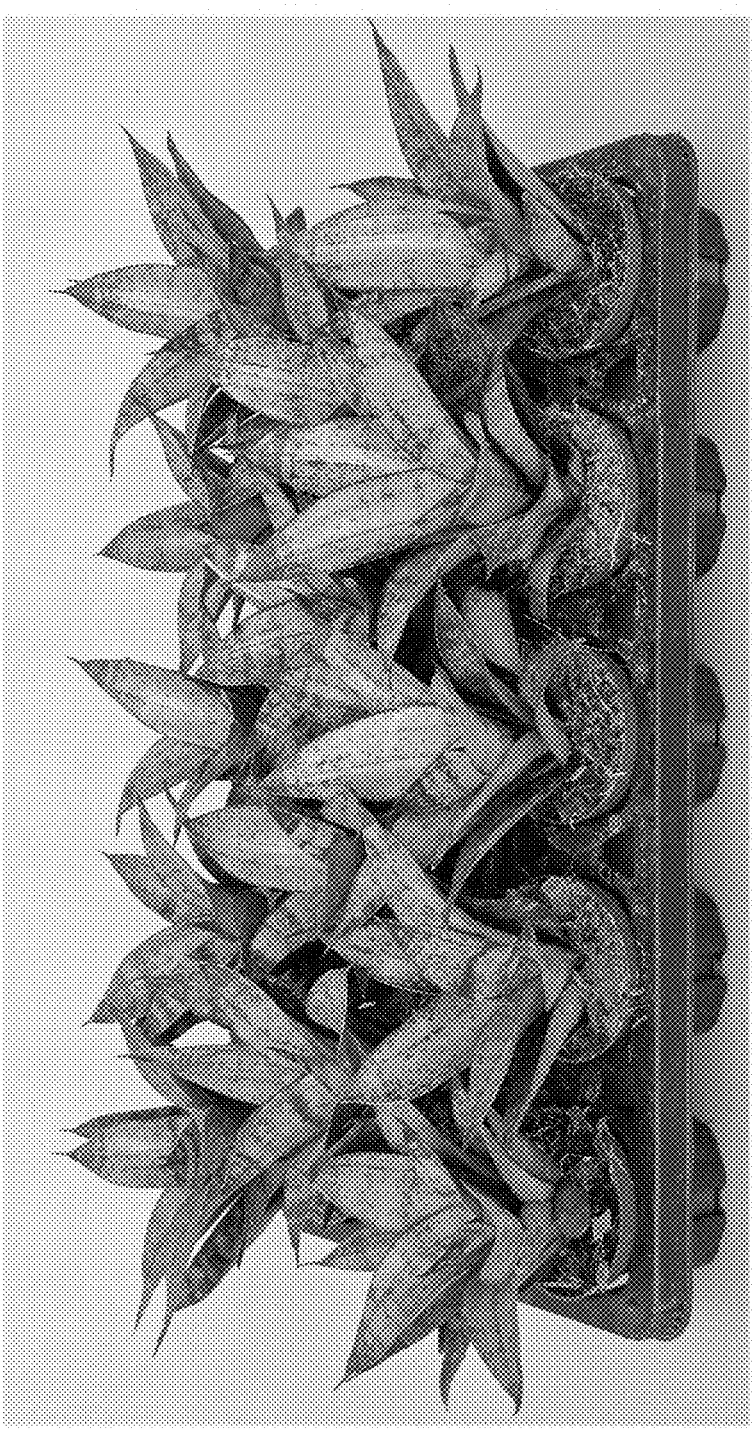
Figure 6:
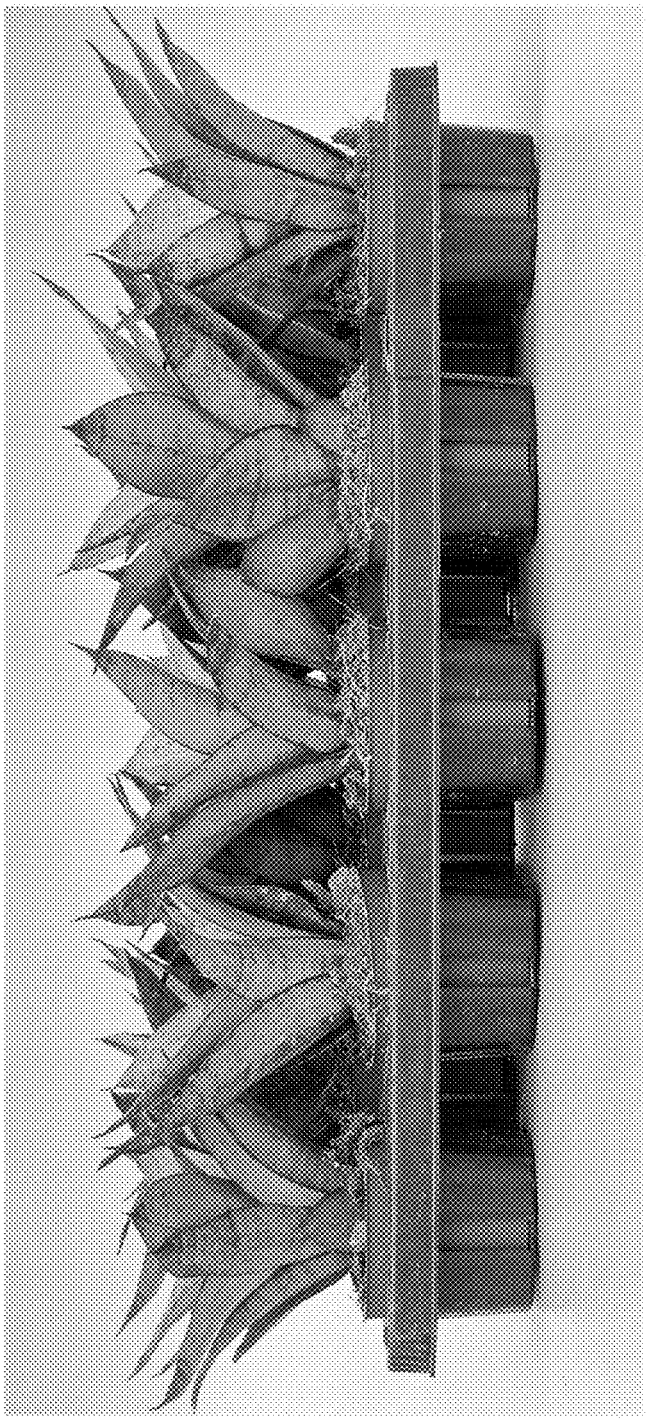
Figure 7:
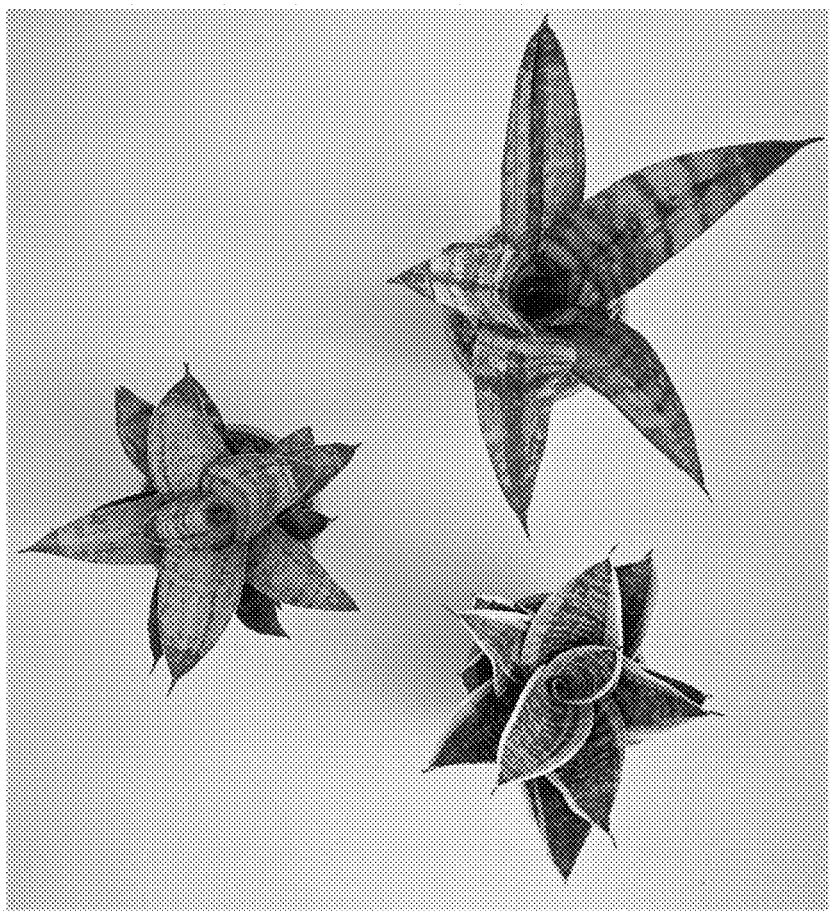
FIG. 7, shows *Sansevieria trifasciata* 'Hahnii Jade Marginata', the parental variety—(bottom left) and *Sansevieria* 'Frozen' (bottom right) both compared with the new cultivar, *Sansevieria trifasciata* 'Hansoti48' (top). Plants are 3 to 4 months old.
Figure 8:
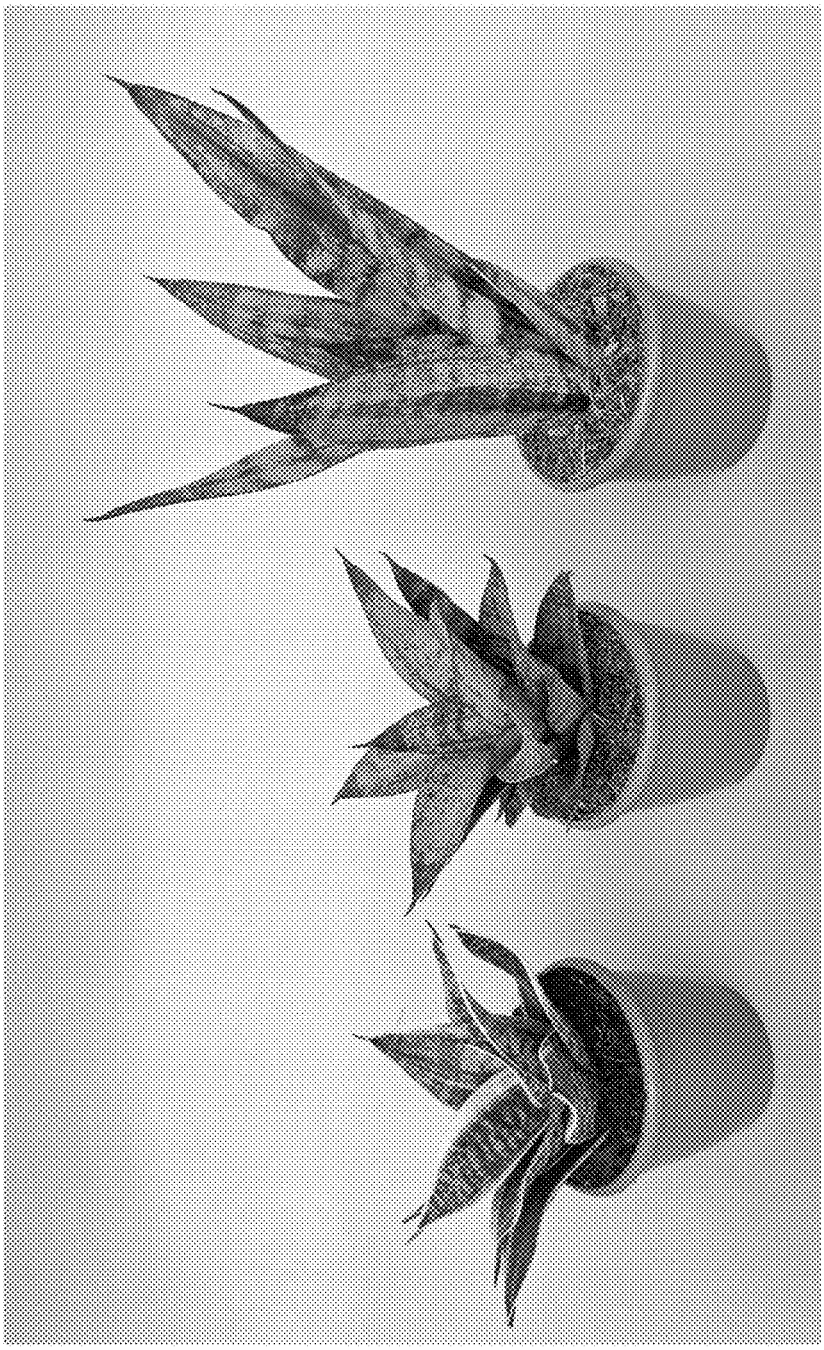
FIG. 8 shows *Sansevieria trifasciata* 'Hahnii Jade Marginata', the parental variety, (left) and *Sansevieria* 'Frozen' (right) both compared with the new cultivar, *Sansevieria trifasciata* 'Hansoti48' (center). Plants are about 3 months old.
Figure 9:
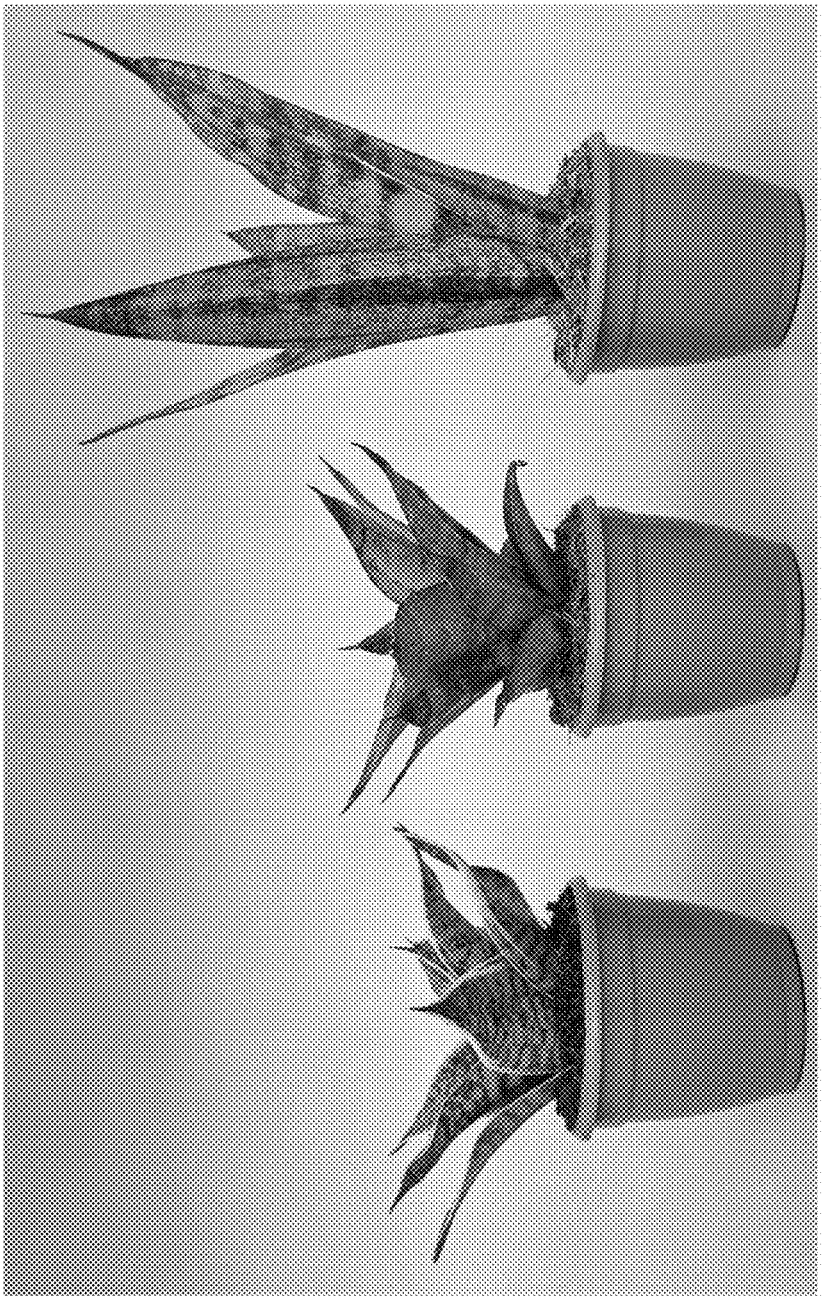

FIG. 9: Show the parent plant—*Sansevieria trifasciata* 'Hahnii Jade Marginata' (left) as well as the other comparable variety *Sansevieria trifasciata* 'Frozen' (right)—alongside a plant of 'HANSOTI48' (center) to compare the three, from two angels to show all aspects of the plants.

Figure 10:
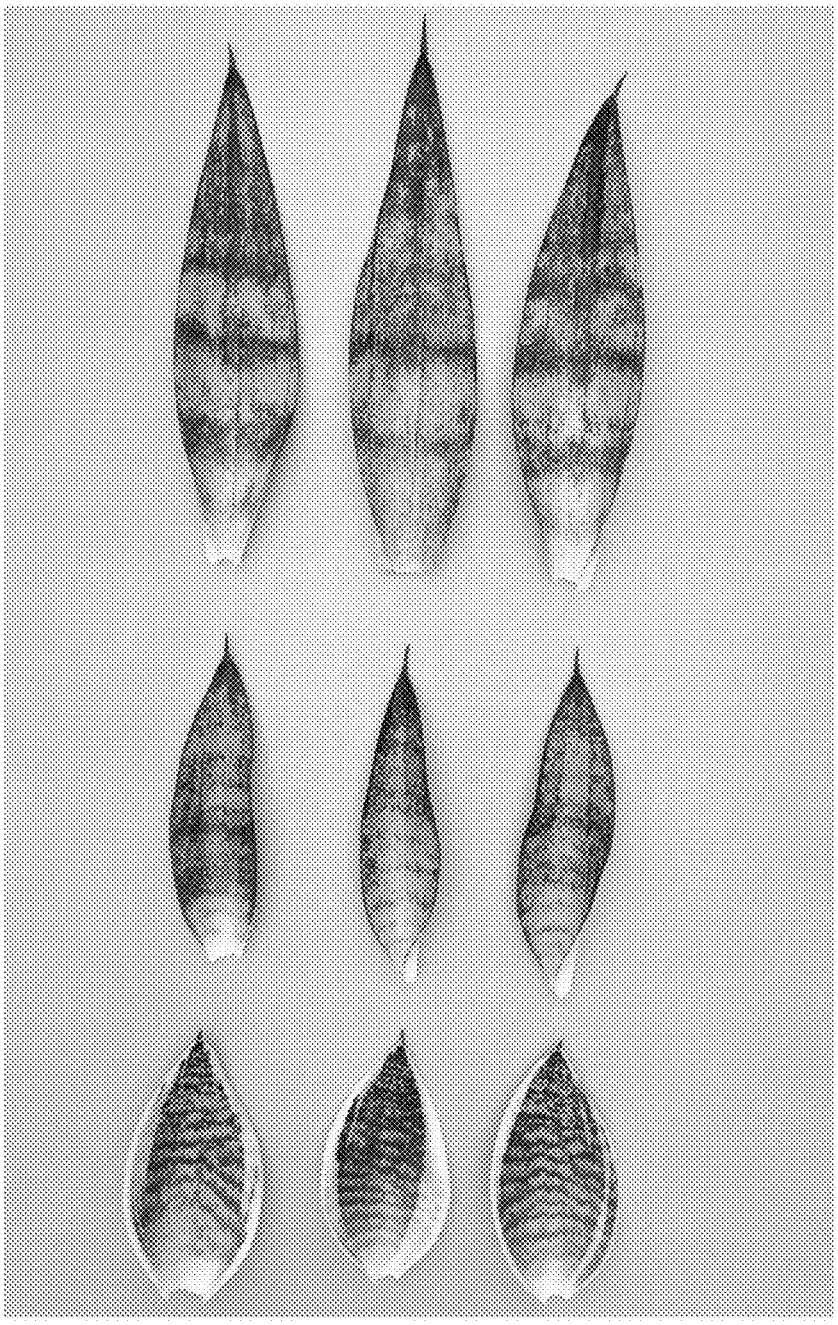

FIG. 10: Shows a comparison of adaxial, or top view of individual leaves of *Sansevieria* 'Hahnii Jade Marginata' (bottom), the parental variety and the comparable variety *Sansevieria trifasciata* 'Frozen' (top) side by side with leaves of *Sansevieria* 'HANSOTI48', (center) the difference in variegation/markings between the parent cultivar (*Sansevieria* 'Hahnii Jade Marginata') and 'Hansoti48' is obvious and so is the pattern and size difference between the comparable *Sansevieria trifasciata* 'Frozen' and 'Hansoti48'.

Figure 11:
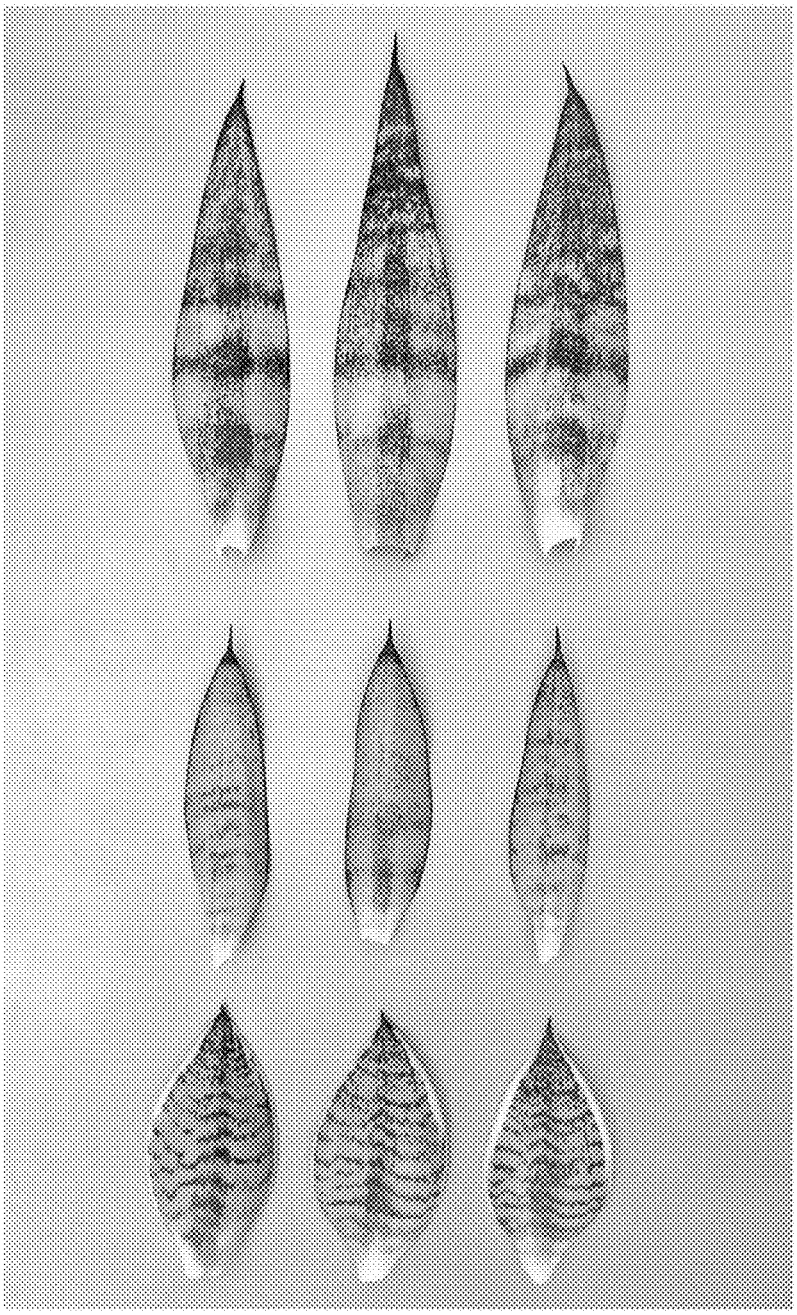

FIG. 11: Bottom or abaxial surface of individual leaves of *Sansevieria trifasciata* 'Hahnii Jade Marginata' (bottom)—the parental variety—and leaves of the other comparable variety—*Sansevieria trifasciata* 'Frozen' (top)—side by side with leaves of the new variety, *Sansevieria trifasciata* 'HANSOTI48' (middle).

DETAILED BOTANICAL DESCRIPTION

The new *Sansevieria* 'HANSOTI48' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI48' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertiliser of 13:11:11 Type 360-days release at 1 kilo/cubic meter of media, liquid feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2007) except where general colors of ordinary significance are used. It should be noted that colors in *Sansevieria* are somewhat variable depending on light levels, nutrition balance, age of plant and other factors. The variety 'HANSOTI48' has, apart from the unusual overall silvery-green look, two major distinctive features compared to its parent plant—there is no light golden yellow border band running along the edge of the and the typical transverse banding of *Sansevieria trifasciata* is much less prominent.

The photographs and descriptions were taken during the monsoon season in Asle, District Satara, Maharashtra State, India when outdoor day and night temperatures were 25° C. to 30° C. The age of the plants described is 3-4 months from rooted liners.

Botanical classification: *Sansevieria trifasciata* 'HANSOTI48'.

General information:

*Parentage*.—*Sansevieria trifasciata* 'Hahnii Jade Marginata', unpatented.

*Optimal growth conditions*.—

*Light intensities*.—High adaptability to outdoor or indoor conditions but needs some shade in hot climates. Shade levels of 35% to 75% depending on season to give maximum light intensity of 350 to 500 μmol/m2/s.

*Temperature*.—Day: 25° C. to 35° C. Night: 15° C. to 25° C.

*Temperature tolerance*.—Tolerant to a low temperature of about 6° C. and a high temperature of 39° C. and above — very heat tolerant.

*Fertilization*.—Constant feed of 100 ppm N, 20 ppm P and 100 ppm K is used along with micronutrients with occasional leaching. Media incorporation of Nutricote 13:11:11 Type 360 days release at 1 kg/cubic meter of media.

*Growth regulators*.—Not necessary for growth, however rooting hormone aids in rapid and prolific rooting of offsets.

Propagation:

*Typical*.—Vegetative, by side suckers which come true to type. Does not come true from leaf cuttings.

*Rooting habit and description*.—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots*.—25 to 30 days at 25° C. to 30° C.

*Time to produce a rooted liner*.—About 45 days at 25° C. to 30° C.

*Time to produce ready* 12 *cm potted plant from liner*.—About 10 to 12 weeks at 25° C. to 30° C.

Plant:

*General appearance and form*.—Monocot; leaf bases arranged in a rosette around growth point.

*Height*.—About 14 to 16 cm when grown in 12 cm pots.

*Spread*.—About 18 to 22 cm when grown when grown in a 12 cm size container.

*Growth rate and habit*.—Moderate growth rate, stays compact for a long time. Generally, *Sansevieria trifasciata* 'Hahnii' shape and form but taller than usual for this group.

*Shape*.—Rosette.

*Fragrance*.—None.

*Stem*.—Modified (rhizomes which are fleshy with erect foliage, branching and giving offsets so forming clumps in time).

*Rosette height*.—About 14 to 16 cm height from top of pot when grown in 12 cm size container.

*Rosette diameter*.—About 18 to 22 cm.

*Texture*.—Smooth, waxy.

*Strength*.—Strong and durable.

*Internode length*.—About 1 mm.

Foliage:

*Quantity*.—About 9 to 12 in ready to sell plant. Number slowly increases with age as old leaves persist for a long time.

*Arrangement and attachment*.—Single, alternate; leaf bases arranged stiffly in a rosette around central growth point.

*Leaf length*.—About 14 to 16 cm, full-size leaf.

*Leaf width*.—About 4 to 6 cm, full-size leaf.

*Overall shape of leaf*.—Lanceolate.

*Apex shape*.—Acute, triangular and aristate, with soft tip.

*Base shape*.—Plane.

*Margin*.—Sharp, smooth.

*Texture*.—Upper Surface: Smooth and waxy texture.

*Texture*.—Under Surface: Smooth and waxy texture.

*Pubescence*.—None.

*Color of mature leaf, upper surface*.—Basal dark green color near RHS Green 139A, overlaid with silvery green near Greyed-Green 191A, and subdued transverse green banding, Green 139B. No creamy or yellow variegation.

*Margins*.—Very thin dark green band, Green 139A along outer edge.

*Crossbanding*.—Typical crossbanding as seen in most *Sansevieria trifasciata* but in this case it's the base dark green color, not very prominent, of color similar to RHS Green 139A.

*Color of mature leaf, lower surface*.—Much more uniform silvery green, Greyed-Green 194D with broad central dark green of N138B towards the proximal end of the leaf and broader lighter bands. Margin: the edge dark green band, Green 139A is thin and continuous along the outer edge of leaf on both sides.

*Venation pattern*.—Longitudinal/parallel leaf shape.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Occasionally shows *Anthracnose* and leaf spots but largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI48' as herein illustrated and described.

* * * * *